United States Patent [19]

Hunter et al.

[11] 4,347,495
[45] Aug. 31, 1982

[54] METHOD OF DETECTING OXYGEN AND AN OXYGEN SENSOR THEREFOR

[75] Inventors: Donald N. Hunter, Bognor Regis; Richard J. Brook, Leeds, both of England

[73] Assignee: Rosemount Engineering Company Limited, West Sussex, England

[21] Appl. No.: 205,953

[22] PCT Filed: Jan. 31, 1980

[86] PCT No.: PCT/GB80/00017
§ 371 Date: Sep. 30, 1980
§ 102(e) Date: Sep. 23, 1980

[87] PCT Pub. No.: WO80/01610
PCT Pub. Date: Aug. 7, 1980

[30] Foreign Application Priority Data

Jan. 31, 1979 [GB] United Kingdom ............... 7903377

[51] Int. Cl.³ .............................................. H01L 7/00
[52] U.S. Cl. ..................................... 338/34; 252/518; 252/521

[58] Field of Search ................. 338/34; 252/518, 521; 73/27 R; 422/98; 264/61

[56] References Cited

U.S. PATENT DOCUMENTS

| | | | |
|---|---|---|---|
| 3,695,848 | 10/1972 | Taguchi | 73/27 R |
| 3,932,246 | 1/1976 | Stadler et al. | 73/27 R X |
| 4,007,435 | 2/1977 | Tien | 338/34 |
| 4,045,764 | 8/1977 | Ichinose et al. | 338/34 |
| 4,086,556 | 4/1978 | Nitta et al. | 338/34 X |

FOREIGN PATENT DOCUMENTS 2331015 6/1977 France.

*Primary Examiner*—C. L. Albritton
*Attorney, Agent, or Firm*—Kinney, Lange, Braddock, Westman and Fairbairn

[57] ABSTRACT

An oxygen sensing element has a body of chromium-rich zinc chromite and electrodes in contact with it for sensing the electrical resistance. At elevated temperatures, the resistance varies with oxygen concentration. A rare earth oxide dopant, preferably 15% mole percent Lanthanum 10 oxide, stabilizes and improves performance.

12 Claims, 1 Drawing Figure

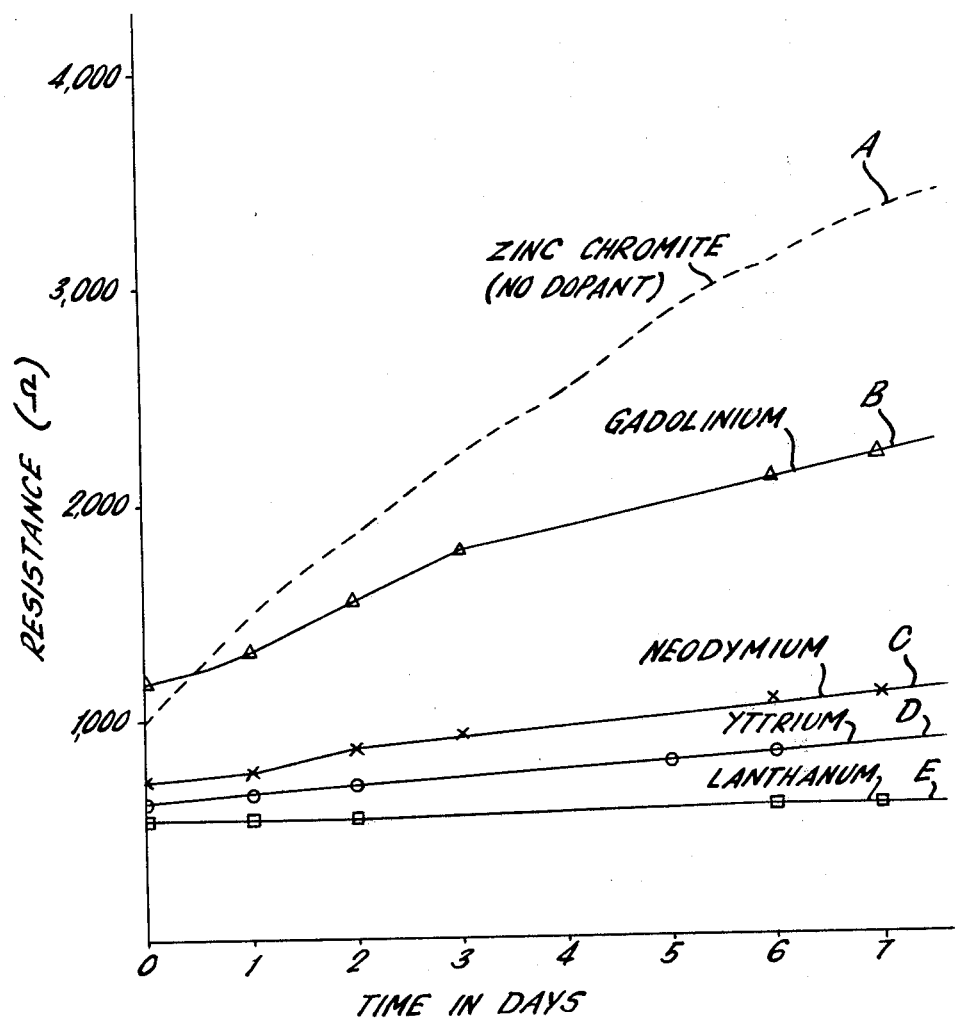

METHOD OF DETECTING OXYGEN AND AN OXYGEN SENSOR THEREFOR

The present invention is concerned with detecting the concentration of oxygen in a gas mixture. It is known to detect oxygen concentration using an oxygen sensor comprising an electrically conducting oxide material the resistance of which depends on the concentration of oxygen in the ambient atmosphere of the sensor. Known oxygen responsive materials for such sensors are based on titanium oxide, zinc oxide, and cobalt oxide. In order to use the sensor, the material is heated to an elevated temperature at which the resistance of the material becomes responsive to the oxygen concentration in the atmosphere, and then the resistance of the material is monitored and provides an indication of the oxygen concentration. Devices of this kind, have various drawbacks. The temperature at which the oxygen responsive materials become effectively responsive to oxygen concentration to be relatively high and difficulty is experienced in keeping the resistance values of the materials stable. Often the resistances of the materials when in a constant oxygen concentration tend to drift upwards in value when the materials are held at the elevated operating temperature for an extended period of time. Also, phase changes can occur in the materials used which degrade the sensitivity of the materials.

According to the present invention, there is provided a sensing element for an oxygen detector, comprising a body of chromium-rich zinc chromite, and means for making electrical contact with the body of zinc chromite to sense its electrical resistance.

The invention also provides a method of detecting oxygen concentration comprising providing a body of chromium rich zinc chromite, heating the body to a temperature at which the resistance of the material of the body is responsive to variations in oxygen concentration in the ambient atmosphere of the body, and measuring the resistance of the material.

Stoichiometric zinc chromite ($Zn Cr_2 O_4$) has a characteristic brown colour, and its electrical resistance does not respond to changes in ambient oxygen concentration. Zinc chromite can also be prepared in which the molar ratio of chromium to zinc is greater than 2. Even very small amounts of excess chromium, for example as little as 0.1% molar excess or less, confer on the compound a characteristic green colour, and the property that the compound's electrical resistance at elevated temperature is responsive to oxygen concentration.

It has been found that chromium rich zinc chromite exhibits useful variations in resistance with oxygen concentration at temperatures as low as 400° C.

In a preferred form of the invention, the chromium-rich zinc chromite of the body has an amount of excess chromium above the solid solution limit of the various oxides of chromium produced in the zinc chromite lattice. Good results have been obtained with zinc chromite having approximately 0.2% molar excess of chromium. Zinc chromite may be prepared by a variety of known reactions, of which the preferred is the reaction of $(NH_4)_2 CrO_7$ with $ZnCl_2$;

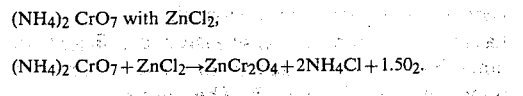

The desired stoichiometry of the product may be ensured by appropriate adjustment of the ratio of the starting materials, so that there is a slight excess of Chromium over that which would be required for the theoretical reaction.

Pure chromium rich zinc chromite has been found to suffer from some instability of resistance and the resistance at constant oxygen concentration has been found to rise progressively over a period of days if the material is kept at an elevated temperature.

Preferably, the material includes up to 25 mole percent of a rare earth oxide. The addition of the rare earth dopant was found to enhance greatly the stability of resistance of the doped material with time and also, at least in some cases, to improve the responsiveness or sensitivity of the material to changes in oxygen concentration. Oxides of Gadolinium Neodymium, Yttrium and Lanthanum all exhibited improved stability, but Lanthanum is preferred, providing not only substantial stability of resistance over a period of at least seven days, but also markedly improved responsiveness to oxygen concentration. The preferred concentration of the rare earth oxide dopant is between 5 and 20 mole percent, and especially preferred is about 15 mole percent.

It should be appreciated that the rare earth "oxide" may be present in the material as an identifiable "chromate" phase (e.g. Lanthanum chromate). X-ray diffraction analysis of a preferred material has indicated the presence of three phases: $Cr_3O_4$, $LaCrO_3$ and $ZnCr_2O_4$. The exact mechanism by which the incorporation of a rare earth dopant stabilizes the resistance of the material is not known, but it is believed that it does in fact form a second phase of the rare earth chromate, which helps to suppress the vaporisation of zinc compounds.

The rare earth oxide deposit may be introduced by including a rare earth oxide among the reactants for the preparation of the chromium-rich zinc chromite. The rare earth oxide is preferably used in amounts of up to 25 mole percent based on the final weight of the doped material.

Various structural and electrical arrangements are known for oxygen sensors of the kind described, which enable the temperature of the responsive material to be raised to and held at the desired level, and the resistance of the material to be measured. Any of these known structures and arrangements may be used in the present invention.

In a preferred embodiment, however, the sensor comprises a substrate of insulating material, a pair of spaced electrodes on a surface of the substrate, a layer of the chromium-rich zinc chromite over said surface with the electrodes, means for heating the substrate and layer to an elevated temperature at which the chromium-rich zinc chromite is responsive to oxygen concentration, and means for connecting the electrodes to a measuring circuit for measuring the resistance between the electrodes.

In a further aspect, the invention provides a novel composition of matter comprising chromium-rich zinc chromite including up to 25% mole percent of a rare earth oxide.

BRIEF DESCRIPTION OF THE DRAWING

The accompanying FIGURE is a graphical representation of the drift in resistance between the electrodes of oxygen sensors using various different responsive materials.

Examples of the present invention will now be described.

EXAMPLE 1

Ammonium dichromate 12.6 grams, and 6.8 grams anhydrous zinc chloride were ground together in a mortar and pestle. The mixture was heated to 300° C. in a large silica dish; a reaction occurring with a swelling of the mix to approximately ten times its starting volume. The light green reaction product was fragmented into the bottom of the dish and heated slowly to 1,000° C. (over 1 hour) and held at 1,000° C. for one hour. After cooling, grinding, and bottling, the X-ray diffraction pattern of the resulting material was checked and the product was found to be zinc chromite with a spinel structure. The X-ray d values were 2.944, 2.512, 2.083, 1.699, 1.605 and 1.473.

To test the zinc chromite material, a pair of platinum electrodes printed on 3 mm square alumina substrate were used. The electrodes were spaced apart on the substrate and each electrode was shaped as a comb with the teeth of the two combs interleaved. The electrodes were bonded to nickel wire leads. The zinc chromite material was ground to a paste with a little water and painted on to the interleaved electrodes on the alumina substrate. The painted substrate was then placed in a tube and heated to 500° C. When a gentle stream of air was passed down the tube over the painted substrate, the resistance between the electrodes was measured as 680 ohms. When a gentle stream of nitrogen was passed down the tube, the resistance was measured as 870 ohms, providing a percentage difference of about 28 percent.

EXAMPLE 2

The same preparation of zinc chromite was carried out as in Example 1, but in this example, 0.815 grams of lanthanum oxide (5 mole percent) was included with the original reactants, ammonium dichromate and zinc chloride.

The resulting paste was brushed onto an identical substrate with platinum electrodes and the resistance between the electrodes at 500° C. in a gentle stream of air was measured as 540 ohms, and in a gentle stream of nitrogen as 940 ohms, a percentage difference of 74 percent.

EXAMPLE 3

The same preparation of zinc chromite was carried out as in Example 1, but in this example, 2.45 grams of lanthanum oxide (15 mole percent) was included with the original reactants. Testing the resulting product in the same way as in example 1, the resistance between the electrodes at 500° C. in a gentle stream of air was measured as 440 ohms and in a gentle stream of nitrogen as 870 ohms, a percentage difference of 98 percent.

EXAMPLE 4

The same preparation of zinc chromite was carried out as in Example 1, but in this example 2.52 grams of neodymium oxide (15 mole percent) was added to the original reactants. Testing the resulting material as in the previous examples, the resistance between the electrodes at 500° C. in a gentle stream of air was measured as 1830 ohms, and in a gentle stream of nitrogen as 2900 ohms, a percentage difference of 58.5 percent.

EXAMPLE 5

The same preparation of zinc chromite was carried out as in Example 1, but in this example 2.72 grams of gadolinium oxide (15 mole percent) was included with the original reactants. Testing the resulting material in the same way as in the previous examples, the resistance between the electrodes at 500° C. in a gentle stream of air was measured as 3300 ohms, and in a gentle stream of nitrogen as 4800 ohms, a percentage difference of 45 percent.

EXAMPLE 6

The same preparation of zinc chromite was carried out as in Example 1, but in this example, 1.695 grams of yttrium oxide (15 mole percent) was added to the original reactants. Testing the resulting material in the same way as in the previous examples, the resistance between the electrodes at 500° C. in a gentle stream of air was measured as 1050 ohms, and in a gentle stream of nitrogen as 1430 ohms, a percentage difference of 36.2 percent.

As mentioned previously, it is desirable that the resistance of the oxygen responsive material used in an oxygen sensor is stable over a period of time, and does not tend to drift upwards if the sensor is maintained in a constant oxygen concentration at the elevated operating temperature. The abscissa of the graph is the time in days for which the sensor was kept at 500° C. in air, and the ordinate is the resistance measured between the electrodes of the sensor. The dotted curve A in the graph, indicates the drift in resistance with time of a sensor using a responsive material comprising plain chromium rich zinc chromite with no rare earth oxide dopant. Curve B shows the drift of a chromium rich zinc chromite doped with 15 molepercent gadolinium oxide. Curve C shows the drift of a sensor with chromium rich zinc chromite doped with 15 molepercent neodymium oxide. Curve D shows the drift of a sensor with chromium rich zinc chromite doped with 15 molepercent yttrium oxide and Curve E shows the drift of a sensor with chromium rich zinc chromite doped with 15 molepercent lanthanum oxide.

In each case, the chromium-rich zinc chromite was made in the manner described in Example 1 above with the appropriate dopant added to the reactants.

It is quite apparent from the graph that the drift performance of the material doped with lanthanum oxide is superior, exhibiting substantially no variation in resistance over a period of seven days at 500° C. in a constant stream of air.

As mentioned previously, the chromium rich zinc chromite materials described herein can be used in any of the known structural and electrical arrangements for oxygen sensors. However, a preferred embodiment comprises a substrate of insulating material, such as alumina, in the form of a substantially flat plate. On one side of the plate there are printed a pair of spaced electrodes which may take the form of two combs with their teeth interleaved or interdigitated with one another. Leadout wires are connected to the respective electrodes and the oxygen responsive material based on chromium rich zinc chromite is provided as a coating over the electrodes. On the reverse face of the substrate is provided a path of an electrically conductive material having a temperature responsive coefficient of resistance. Provision is made for connecting leadout wires to opposite ends of this path. The path may be formed of a vitreous material containing platinum particles and exhibiting a temperature responsive resistance similar to that of bulk platinum. In operation, the conducting path on the reverse side of the substrate is connected in an electrical circuit arranged to supply a current through the conducting path to heat the device to the desired operating temperature, typically 500° C. The temperature of the device can be monitored by measuring the resistance of the conducting path. The resistance between the interdigitated electrodes covered with the zinc chromite material can then be monitored in a second electrical circuit to provide an indication of the concentration of the oxygen in the ambient atmosphere of the device.

We claim:

1. A sensing element for an oxygen detector, comprising a body of chromium-rich zinc chromite having in excess of a stoichiometric proportion of chromium in zinc chromite, and means for making electrical contact with the body of zinc chromite to sense its electrical resistance.

2. An element as claimed in claim 1, wherein chromium is present in approximately 0.2% molar excess of the stoichiometric proportion needed to produce zinc chromite.

3. An element as claimed in claim 1 or claim 2, wherein the chromium-rich zinc chromite contains up to 25 mole percent of a rare earth oxide dopant (calculated as MO based on the total weight of the doped material, wherein M is the rare earth metal).

4. An element as claimed in claim 3 wherein the chromium-rich zinc chromite contains between 5 and 20 mole percent of a rare earth oxide dopant.

5. An element as claimed in claim 4 wherein the chromium-rich zinc chromite contains about 15 mole percent of a rare earth oxide dopant.

6. An element as claimed in claim 3 wherein the rare earth oxide of the dopant is lanthanum oxide.

7. An element as claimed in claim 1 wherein the means for making electrical contact includes a pair of electrical conductors provided on the surface of an electrical insulator, the conductors being bridged by said body of chromium-rich zinc chromite.

8. An element as claimed in claim 7 wherein the conductors are interdigitated combs.

9. An element as claimed in claim 7 or claim 8 and comprising a substrate of insulating material, a pair of spaced electrodes on a surface of the substrate, a layer of the chromium-rich zinc chromite over said surface with the electrodes, means for heating the substrate and layer to an elevated temperature at which the chromium-rich zinc chromite is responsive to oxygen concentration, and means for connecting the electrodes to a measuring circuit for measuring the resistance between the electrodes.

10. A method of detecting oxygen concentration comprising providing a body of chromium rich zinc chromite having in excess of a stoichiometric proportion of chromium in zinc chromite, heating the body to a temperature at which the resistance of the material of the body is responsive to variations in oxygen concentration in the ambient atmosphere of the body, and measuring the resistance of the material.

11. A method as claimed in claim 10 wherein a rare earth oxide dopant is introduced by including a rare earth oxide among the reactants for the preparation of the chromium-rich zinc chromite.

12. Chromium-rich zinc chromite having in excess of a stoichiometric proportion of chromium in zinc chromite including up to 25 mole percent of a rare earth oxide.

* * * * *